United States Patent [19]

Webber

[11] 4,196,207

[45] Apr. 1, 1980

[54] PROCESS FOR CONTROLLING ERADICATING OR PREVENTING INFESTATIONS OF ANIMALS BY IXODID TICKS

[75] Inventor: Lionel G. Webber, D'Aguilar, Australia

[73] Assignee: ICI Australia Limited, ralia

[21] Appl. No.: 905,038

[22] Filed: May 9, 1978

[30] Foreign Application Priority Data

May 23, 1977 [AU] Australia ............................ PD0189

[51] Int. Cl.² .......................................... A61K 31/505
[52] U.S. Cl. ...................................... 424/251; 544/278
[58] Field of Search ........................ 424/251; 544/278

[56] References Cited

U.S. PATENT DOCUMENTS 4,076,817  2/1978  Acheson et al. ..................... 544/278

OTHER PUBLICATIONS

Cox et al.—Chem. Abst. vol. 87 (1977) p. 128,906p.

Primary Examiner—Sam Rosen
Attorney, Agent, or Firm—Cushman, Darby & Cushman

[57] ABSTRACT

A process for the prevention of infestation by Ixodid ticks, or for the control or eradication of infestations of Ixodid ticks, which process comprises applying to the media to be protected or to the infested media an effective amount of a composition comprising as active ingredient a thienopyrimidine derivative of general formula I:

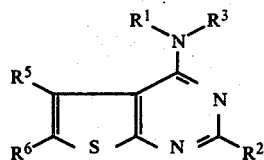

wherein
$R^1$ is chosen from alkyl optionally substituted with hydroxy, methoxy, cycloalkyl, aryl, heteroaryl, and heterocycloalkyl groups; alkenyl; alkynyl; cycloalkyl;
$R^3$ is chosen from hydrogen, alkyl and acyl; or $R^1$ and $R^3$ together form a saturated or unsaturated alkylene or heteroalkylene bridging group;
$R^2$ is chosen from hydrogen, hydroxy, mercapto, halo, cyano, optionally substituted-amino, optionally substituted hydrazino, alkyl, alkenyl, alkynyl, alkoxy, alkylthio, cycloalkyl, aralkyl, aryl and trifluoromethyl;
$R^5$ and $R^6$ are independently chosen from hydrogen, optionally substituted alkyl, halogen and aryl;
or $R^5$ and $R^6$ together form a saturated alkyl bridging group;
or an optical isomer thereof; or a tautomer thereof; or a salt thereof; and a carrier therefor.

20 Claims, No Drawings

PROCESS FOR CONTROLLING ERADICATING OR PREVENTING INFESTATIONS OF ANIMALS BY IXODID TICKS

This invention relates to a process for the control or eradication of Ixodid ticks and more particularly to a process for the treatment of animals to control or eradicate Ixodid ticks or to protect the animals from infestation by Ixodid ticks.

Ixodidae, or hard ticks, are responsible for the maintenance and propagation of a great many human and animal diseases throughout the world. The species of most economic importance include the Boophilus spp., Rhipicephalus spp., Ixodes spp., Hyalomma spp., Amblyomma spp. and Dermacentor spp.

In Australia a problem of considerable economic importance is the control of ticks which infest cattle. Of these ticks the species *Boophilus microplus*, commonly known as the cattle tick, is responsible for the greatest economic losses in cattle production.

In the past "susceptible" or "non-resistant" strains of cattle tick have been controlled by means of sprays using as active ingredients certain chemicals such as carbamates, chlorinated hydrocarbons or organophosphates. However more recently it has been found that certain strains of cattle ticks have emerged and are now wide spread in Australia and elsewhere and are spreading further and which are not affected by certain of the broad spectrum tickicides normally used for this purpose. These strains are known as "resistant" strains of cattle ticks and represent a most serious problem to the Australian cattle industry.

A typical "susceptible" strain is the "Yeerongpilly" strain which is widely distributed and is controlled readily with commercial tickicides such as 1-naphthyl N-methylcarbamate, dichlorodiphenyltrichloroethane (DDT) or a wide range of organophosphorus tickicides including those available commercially under the registered trade names of "Asuntol", "Dioxathion", "Dursban", "Ethion", "Nexagan" S or "Solgard". It is used by all authorities in Australia as the "susceptible" reference standard against which the degree of resistant strains is measured.

A typical resistant strain is the "Biarra" strain also known as the "Esk" or "Anderson" strain, and it has become increasingly resistant to organophosphorus tickicides with the passage of time since it was isolated in the Esk district of Queensland, Australia in 1966. Other strains of cattle tick which are resistant to organophosphorus tickicides include the so called "Mount Alford" strain and the "Mackay" strain. Certain strains of cattle tick may become resistant to treatment with tickicides after prolonged treatment therewith. For example whilst DDT was effective as a tickicide when it was first used for the purpose, there are now strains of tick which are immune to treatment with DDT at concentrations which are economic. It is highly desirable that new tickicides be developed so that the cattle tick has little or no resistance to the tickicides when it is first used. Such tickicides should be effective in controlling and killing cattle ticks of both the "susceptible" strains and the strains which are resistant to tickicides already in use. Unless a tickicide is active against both the "resistant" and "susceptible" strains, the long range effect of treatment in a given treatment area is not to control cattle ticks, but merely to increase the population of the "resistant" strain in relation to that of the "susceptible" strain.

We have now found that certain thienopyrimidine derivatives are active as tickicides and are particularly useful in the treatment of animals to prevent infestation by, or to control or eradicate infestations of, Ixodid ticks.

Accordingly we provide a process for the prevention of infestation by Ixodid ticks, or for the control or eradication of infestations of Ixodid ticks, which process comprises applying to the media to be protected, or to the infested media, an effective amount of a composition comprising as active ingredient a thienopyrimidine derivative of general formula I:

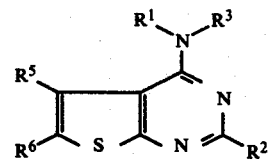

wherein $R^1$ is chosen from alkyl optionally substituted with hydroxy, methoxy, cycloalkyl, aryl, heteroaryl and heterocycloalkyl groups; alkenyl; alkynyl; cycloalkyl;

$R^3$ is chosen from hydrogen, alkyl and acyl; or $R^1$ and $R^3$ together form a saturated or unsaturated alkylene or heteroalkylene bridging group;

$R^2$ is chosen from hydrogen, hydroxy, mercapto, halo, cyano, optionally substituted amino, optionally substituted hydrazino, alkyl, alkenyl, alkynyl, alkoxy, alkylthio, cycloalkyl, aralkyl, aryl and trifluoromethyl;

$R^5$ and $R^6$ are independently chosen from hydrogen, optionally substituted alkyl, halogen and aryl;

or $R^5$ and $R^6$ together form a saturated alkyl bridging group;

or an optical isomer thereof; or a tautomer thereof; or a salt thereof; and a carrier therefor.

In a preferred embodiment the invention provides a process as stated above wherein in the thienopyrimidine derivative of general formula I:

$R^1$ is chosen from straight or branched chain $C_1$ to $C_{20}$ alkyl optionally substituted with hydroxy and/or methoxy; $C_2$ to $C_{20}$ alkenyl; $C_2$ to $C_{20}$ alkynyl; $C_3$ to $C_8$ cycloalkyl; $C_3$ to $C_8$ cycloalkylmethyl; arylmethyl, 2-arylethyl and 1-arylethyl wherein aryl is chosen from furyl, thienyl, pyridyl, naphthyl, benzimidazolyl and phenyl optionally substituted with one or more substituents chosen from halogen, $C_1$ to $C_6$ alkoxy, and $C_1$ to $C_6$ alkyl;

$R^3$ is chosen from hydrogen, $C_1$ to $C_6$ alkyl and $C_1$ to $C_6$ alkanoyl;

or $R^1$ and $R^3$ together form a saturated or unsaturated alkylene bridging group in which one or more carbons are optionally replaced by oxygen or nitrogen;

$R^2$ is chosen from hydrogen, hydroxy, mercapto, halo, cyano, $C_1$ to $C_6$ alkylamino, $C_2$ to $C_{12}$ dialkylamino, hydrazino, $C_1$ to $C_6$ alkyl, $C_1$ to $C_6$ alkoxy, $C_1$ to $C_6$ alkylthio, phenyl optionally substituted with one or more halogen atoms, and trifluoromethyl;

$R^5$ is chosen from hydrogen and $C_1$ to $C_6$ alkyl;

$R^6$ is chosen from hydrogen, $C_1$ to $C_6$ alkyl, halogen and phenyl;

or $R^5$ and $R^6$ together form a $C_2$ to $C_6$ alkylene bridging group.

In a more preferred embodiment the invention provides a process as stated above wherein in the thienopyrimidine of general formula I:

$R^1$ is chosen from straight or branched chain alkyl containing from 4 to 20 carbon atoms optionally substituted with hydroxy or methoxy, $C_4$ to $C_{20}$ alkenyl, and 1-phenylethyl;

$R^3$ is chosen from hydrogen, $C_1$ to $C_6$ alkyl and $C_1$ to $C_6$ alkanoyl;

$R^2$ is chosen from hydrogen, $C_1$ to $C_6$ alkyl and phenyl; and $R^5$ and $R^6$ are independently chosen from hydrogen and $C_1$ to $C_6$ alkyl.

In an even more preferred embodiment the invention provides a process as stated above wherein in the thienopyrimidine of general formula I:

$R^1$ is chosen from straight or branched chain alkyl containing from 4 to 20 carbon atoms;

$R^2$ and $R^3$ are chosen from hydrogen and methyl;

$R^5$ and $R^6$ are chosen from hydrogen and methyl provided that $R^6$ is methyl only when $R^5$ is methyl.

The process of the invention is useful as a means for the prevention of infestation by, or for the control of infestations of, Ixodid ticks on media such as buildings and animals such as horses, sheep, dogs and cattle. The process of the invention is particularly useful for the treatment of animals to prevent or control infestations of Ixodid ticks.

Accordingly in yet a further embodiment the invention provides a process for the treatment of animals to prevent infestation by, or to control or eradicate infestations of, Ixodid ticks which process comprises treating said animals with a tickicidally effective amount of a composition comprising as active ingredient a thienopyrimidine derivative of general formula I as hereinbefore defined.

The process of the invention produces high contact activity against various strains of the cattle tick *Boophilus microplus* in the adult, larval and intermediate stages, and both the "susceptible" and "resistant" strains may be controlled. This simultaneous efficacy against both the "susceptible" and "resistant" strains of *Boophilus microplus* is of considerable and increasing economic importance.

Accordingly in a particularly preferred embodiment the invention provides a process for the control or eradication of the cattle tick *Boophilus microplus* which process comprises treating cattle infested with the cattle tick *Boophilus microplus* with a tickicidally effective amount of a composition comprising as active ingredient a thienopyrimidine derivative of general formula I as hereinbefore defined.

Specific examples of the thienopyrimidine derivatives useful in the process of the invention are set forth in Table I below wherein the substituents $R^1$, $R^2$, $R^3$, $R^5$ and $R^6$ refer to the substituents in the thienopyrimidine of general formula I.

TABLE 1

| Compound No. | $R^1$ | $R^2$ | $R^3$ | $R^5$ | $R^6$ | m.p. °C. |
|---|---|---|---|---|---|---|
| 1 | H | H | H | H | H | 235 |
| 2 | $CH_3$ | H | H | H | H | 202 |
| 3 | $CH_2CH_3$ | H | H | H | H | 162 |
| 4 | n-$C_3H_7$ | H | H | H | H | 136 |
| 5 | $CH(CH_3)_2$ | H | H | H | H | 228 |
| 6 | n-$C_4H_9$ | H | H | H | H | 106 |
| 7 | $CH(CH_3)C_2H_5$ | H | H | H | H | 192 |
| 8 | $CH_2$-(2-furyl) | H | H | H | H | 159 |
| 9 | $CH_2C_6H_5$ | H | H | H | H | 185 |
| 10 | n-$C_3H_7$ | H | H | H | $C_6H_5$ | 167 |
| 11 | n-$C_5H_{11}$ | H | H | H | H | 89 |
| 12 | $C_6H_5$ | H | H | H | H | 175 |
| 13 | n-$C_4H_9$ | H | H | H | $C_6H_5$ | 144 |
| 14 | H | H | H | $(CH_2)_4$ | | 263 |
| 15 | $CH_2C_6H_5$ | H | H | $(CH_2)_4$ | | 118 |
| 16 | $CH_2CH(CH_3)_2$ | H | H | H | H | 141 |
| 17 | cyclo hexyl | H | H | H | H | 174 |
| 18 | $CH(CH_3)_2$ | $CH_3$ | H | H | H | 166 |
| 19 | $(CH_2)_2OH$ | H | H | H | H | 179 |
| 20 | n-$C_6H_{13}$ | H | H | H | H | 59 |
| 21 | $CH(CH_3)C_2H_5$ | $CH_3$ | H | H | H | 179 |
| 22 | $CH_3$ | H | $CH_3$ | H | H | 76 |
| 23 | $CH_2C(CH_3)_3$ | H | H | H | H | 142 |
| 24 | $CH_2C_6H_5$ | $CH_3$ | H | H | H | 148 |
| 25 | $C(CH_3)_3$ | H | H | H | H | 172 |
| 26 | $C_2H_5$ | $CH_3$ | H | H | H | 162 |
| 27 | $CH_2CH_2C_6H_5$ | H | H | H | H | 189 |
| 28 | $CH_2CH=CH_2$ | H | H | H | H | 124 |
| 29 | cyclo heptyl | H | H | H | H | 128 |
| 30 | $CH(CH_3)C_6H_5$ | H | H | H | H | 132 |
| 31 | $CH_2$-4-pyridyl | H | H | H | H | 182 |
| 32 | $CH(CH_3)CH_2OCH_3$ | H | H | H | H | 153 |
| 33 | $CH(CH_3)CH_2CH(CH_3)_2$ | H | H | H | H | 138 |
| 34 | $CH_2CH(CH_2CH_3)(CH_2)_3CH_3$ | H | H | H | H | 72 |
| 35 | $CH(CH_3)(CH_2)_3CH(CH_3)_2$ | H | H | H | H | 104 |
| 36 | $CH(CH_3)C(CH_3)_3$ | H | H | H | H | 166 |
| 37 | $CH_2CH(CH_3)OH$ | H | H | H | H | 126 |
| 38 | $CH_2CH(OCH_3)_2$ | H | H | H | H | 101 |
| 39 | $CH_2CH_3$ | H | $CH_2CH_3$ | H | H | 73 |
| 40 | $CH(CH_3)(CH_2)_2CH_3$ | H | H | H | H | 120 |
| 41 | $(CH_2)_9CH_3$ | H | H | H | H | 52 |

TABLE 1-continued

| Compound No. | R[1] | R[2] | R[3] | R[5] | R[6] | m.p. °C. |
|---|---|---|---|---|---|---|
| 42 | $CH_2C(OH)(CH_3)_2$ | H | H | H | H | 156 |
| 43 | $CH(CH_3)_2$ | $C_6H_5$ | H | H | H | 142 |
| 44 | $CH(CH_2CH_3)_2$ | H | H | H | H | 151 |
| 45 | $(CH_2)_2C(CH_3)_3$ | H | H | H | H | 135 |
| 46 | cyclo propyl | H | H | H | H | 146 |
| 47 | $CH(CH_3)CH(CH_3)_2$ | H | H | H | H | 134 |
| 48 | $CH(CH_3)CH_2CH_3$ | $C_6H_5$ | H | H | H | 142 |
| 49 | cyclo pentyl | H | H | H | H | 162 |
| 50 | $CH_3$ | H | $C_6H_5$ | H | H | 131 |
| 51 | $CH_2C\equiv CH$ | H | H | H | H | 150 |
| 52 | $CH_3$ | H | $(CH_2)_3CH_3$ | H | H | [b.p. 150° (bath)/ 0.03mm] |
| 53 | $(CH_2)_3OCH_3$ | H | H | H | H | 87 |
| 54 | $CH[CH(CH_3)_2]_2$ | H | H | H | H | 134 |
| 55 | $CH_2C_6H_5$ | $C_6H_5$ | H | H | H | 147 |
| 56 | $CH(CH_3)(CH_2)_4CH_3$ | H | H | H | H | 94 |
| 57 | $(CH_2)_2CH(CH_3)_2$ | H | H | H | H | 124 |
| 58 | $CH_2CH(CH_3)CH_2CH_3$ | H | H | H | H | 110 |
| 59 | cyclo butyl | H | H | H | H | 178 |
| 60 | $(CH_2)_2N(CH_2CH_3)_2$ | H | H | H | H | 88 |
| 61 | $(CH_2)_{11}CH_3$ | H | H | H | H | 61 |
| 62 | $(CH_2)_2OCH_3$ | H | H | H | H | 90 |
| 63 | $CH_2\text{-}3\text{-}Cl\text{—}C_6H_4$ | H | H | H | H | 174 |
| 64 | $CH_2\text{-}2,4\text{-}Cl_2\text{—}C_6H_3$ | H | H | H | H | 233 |
| 65 | $(CH_2)_2N(CH_2CH_3)_2$ | H | H | $CH_3$ | $CH_3$ | 75 |
| 66 | $CH_2\text{-}4\text{-}OCH_3\text{—}C_6H_4$ | H | H | H | H | 153 |
| 67 | $CH_2\text{-}4\text{-}F\text{—}C_6H_4$ | H | H | H | H | 139 |
| 68 | $CH_2CH_2CH_3$ | $C_6H_5$ | H | H | H | 85 |
| 69 | $(CH_2)_5CN$ | H | H | H | H | 73 |
| 70 | $CH_2$-2-benzimidazolyl | H | H | H | H | >300 |
| 71 | $CH_2\text{-}3,4\text{-}Cl_2\text{—}C_6H_3$ | H | H | H | H | 166 |
| 72 | $CH_2\text{-}2\text{-}Cl\text{—}C_6H_4$ | H | H | H | H | 175 |
| 73 | $CH_2\text{-}4\text{-}Cl\text{—}C_6H_4$ | H | H | H | H | 174 |
| 74 | $CH_2$-cyclo hexyl | H | H | H | H | 136 |
| 75 | $CH_2\text{-}3,4\text{-}(OCH_3)\text{—}C_6H_3$ | H | H | H | H | 181 |
| 76 | $(CH_2)_6CH_3$ | H | H | H | H | 53 |
| 77 | cyclo octyl | H | H | H | H | 128 |
| 78 | $(CH_2)_7CH_3$ | H | H | H | H | 65 |
| 79 | $CH(CH_3)\text{-}4\text{-}F\text{—}C_6H_4$ | H | H | H | H | 150 |
| 80 | $CH(C_6H_5)CH_2C_6H_5$ | H | H | H | H | 149 |
| 81 | $CH_2\text{-}4\text{-}CH_3\text{—}C_6H_4$ | H | H | H | H | 144 |
| 82 | $CH(CH_3)_2$ | H | H | H | $CH_3$ | 163 |
| 83 | $CH(CH_3)CH_2CH_3$ | H | H | H | $CH_3$ | 170 |
| 84 | $CH(CH_3)(CH_2)_4CH_3$ | H | H | H | $CH_3$ | 152 |
| 85 | $(CH_2)_2CH_3$ | H | H | H | $CH_3$ | 147 |
| 86 | $CH(C_6H_5)_2$ | H | H | H | H | 107 |
| 87 | $CH(CH_3)_2$ | H | H | $CH_3$ | H | 129 |
| 88 | $CH(CH_3)CH_2CH_3$ | H | H | $CH_3$ | H | 70 |
| 89 | $CH(CH_3)(CH_2)_4CH_3$ | H | H | $CH_3$ | H | 77 [b.p. 190° (bath)/ 0.05 mm] |
| 90 | $CH_2CH(C_6H_5)_2$ | H | H | H | H | 135 |
| 91 | $CH_2$-α-naphthyl | H | H | H | H | 174 |
| 92 | $CH(CH_3)(CH_2)_7CH_3$ | H | H | H | H | 105 |
| 93 | $CH(CH_3)(CH_2)_2CH_3$ | $CH_3$ | H | H | H | 132 |
| 94 | $CH(CH_3)(CH_2)_4CH_3$ | $CH_3$ | H | H | H | 107 |
| 95 | $CH(CH_3)CH(CH_3)CH_2CH_3$ | H | H | H | H | 128 |
| 96 | $CH(CH_3)_2$ | $CF_3$ | H | H | H | 102 |
| 97 | $CH(CH_3)CH_2CH_3$ | $CF_3$ | H | H | H | 73 |
| 98 | $CH(CH_3)(CH_2)_4CH_3$ | $CF_3$ | H | H | H | 85 |
| 99 | $(CH_2)_2CH_3$ | $CF_3$ | H | H | H | 75 |
| 100 | $CH(CH_3)_2$ | $C(CH_3)_3$ | H | H | H | 110 |
| 101 | $C(CH_3)_2CH_2CH_3$ | H | H | H | H | 106 |
| 102 | $CH(CH_3)(CH_2)_2CH(CH_3)_2$ | H | H | H | H | 106 |
| 103 | $CH(CH_3)C_6H_5$ | $C(CH_3)_3$ | H | H | H | 139 |
| 104 | $CH(CH_3)(CH_2)_4CH_3$ | $C(CH_3)_3$ | H | H | H | [b.p. 140° (bath)/ 0.01 mm] |
| 105 | $CH(CH_3)C_6H_5$ | $CF_3$ | H | H | H | 121 |
| 106 | $CH_2\text{-}2,5\text{-}(CH_3)_2\text{—}C_6H_3$ | H | H | H | H | 198 |
| 107 | $CH(CH_3)(CH_2)_3CH_3$ | H | H | H | H | 109 |
| 108 | $CH(CH_3)(CH_2)_6CH_3$ | H | H | H | H | 92 |
| 109 | $CH(CH_3)(CH_2)_5CH_3$ | H | H | H | H | 115 |
| 110 | $CH[CH_2CH(CH_3)_2]_2$ | H | H | H | H | 163 |
| 111 | $CH_2\text{-}2,4\text{-}(OMe)_2\text{—}C_6H_3$ | H | H | H | H | 151 |
| 112 | $CH(CH_3)(CH_2)_4CH_3$ | $C_6H_5$ | H | H | H | 96 |
| 113 | $CH_3$ | $CF_3$ | H | H | H | 134 |
| 114 | $(CH_2)_2CH_3$ | $C(CH_3)_3$ | H | H | H | 93 |
| 115 | $CH(CH_3)CH_2CH_3$ | $C(CH_3)_3$ | H | H | H | 131 |
| 116 | $CH[(CH_2)_2CH_3]_2$ | H | H | H | H | 147 |

TABLE 1-continued

| Compound No. | R¹ | R² | R³ | R⁵ | R⁶ | m.p. °C. |
|---|---|---|---|---|---|---|
| 117 | CH(CH₃)CH₂CH(CH₃)CH₂CH₃ | H | H | H | H | 136 |
| 118 | CH(CH₃)C₆H₅; prepared from (+) amine; R configuration | H | H | H | H | 120 |
| 119 | CH(CH₃)C₆H₅; prepared from (−) amine; S configuration | H | H | H | H | 120 |
| 120 | CH(CH₃)(CH₂)₃N(CH₂CH₃)₂ | H | H | H | H | 73 (monohydrate) |
| 121 | CH(CH₃)₂ | H | H | —(CH₂)₄— | | 135 |
| 122 | CH(CH₃)CH₂CH₃ | H | H | —(CH₂)₄— | | 153 |
| 123 | CH(CH₃)C₆H₅ | H | H | —(CH₂)₄— | | 142 |
| 124 | CH(CH₃)(CH₂)₃CH(CH₃)₂ | H | H | —(CH₂)₄— | | 65 |
| 125* | —(CH₂)₄— | H | (see R¹) | H | H | 90 |
| 126* | —CH=N—CH=CH— | H | (see R¹) | H | H | 177 |
| 127* | —CH=N—CH=N— | H | (see R¹) | H | H | 138 |
| 128* | —CH=CH—CH=N— | H | (see R¹) | H | H | 112 |

*Compounds Nos 125, 126, 127 and 128 have a combined R¹ and R³ bridging group shown complete under heading R¹.

| Compound No. | R¹ | R² | R³ | R⁵ | R⁶ | m.p. °C. |
|---|---|---|---|---|---|---|
| 129 | H | H | NH₂ | H | H | 225 |
| 130 | CH₃ | H | NH₂ | H | H | 173 |
| 131 | H | H | NH₂ | CH₃ | CH₃ | 219 |
| 132 | hydrochloride of compound No. 133 | | | | | 188 |
| 133 | (CH₂)₂OH | H | NH₂ | H | CH₃ | 129 |
| 134 | (CH₃)₂CH | H | H | H | NO₂ | 200 |
| 135 | C₂H₅ | H | C₂H₅ | H | NO₂ | 135 |
| 136 | CH₂C₆H₅ | H | H | H | NO₂ | 214 |
| 137 | CH(CH₃)₂ | Cl | H | H | H | 160 |
| 138 | CH(CH₃)CH₂CH₃ | Cl | H | H | H | 188 |
| 139 | C₂H₅ | Cl | H | H | H | 143 |
| 140 | CH₃ | Cl | H | H | H | 243 |
| 141 | CH₂C₆H₅ | Cl | H | H | H | 170 |
| 142 | CH(CH₃)C₆H₅ | Cl | H | H | H | 165 |
| 143 | CH₂CH(CH₃)₂ | Cl | H | H | H | 109 |
| 144* | —(CH₂)₂O(CH₂)₂— | Cl | (see R¹) | H | H | 124 |
| 145 | CH(CH₃)₂ | imidazolyl | H | H | H | 228 |
| 146 | CH(CH₃)₂ | 1,2,4-triazol-1-yl | H | H | H | 192 |
| 147 | CH(CH₃)₂ | OCH₃ | H | H | H | 173 |
| 148 | CH(CH₃)₂ | NHNH₂ | H | H | H | 131 |
| 149 | CH(CH₃)₂ | morpholino | H | H | H | 173 |
| 150 | CH(CH₃)₂ | pyrazolyl | H | H | H | 198 |
| 151 | CH(CH₃)₂ | 3,5-dimethyl pyrazolyl | H | H | H | 233 |
| 152 | CH(CH₃)₂ | N₃ | H | H | H | 131 |
| 153 | CH(CH₃)₂ | SCH₃ | H | H | H | 128 |
| 154 | CH(CH₃)₂ | piperidino | H | H | H | 139 |
| 155 | CH(CH₃)₂ | SO₂CH₃ | H | H | H | 163 |
| 156 | CH(CH₃)₂ | pyrrolidino | H | H | H | 183 |
| 157 | CH(CH₃)₂ | SOCH₃ | H | H | H | 156 |
| 158 | CH(CH₃)₂ | NHCH₂CH(CH₃)₂ | H | H | H | 98 |
| 159 | CH(CH₃)₂ | CN | H | H | H | 168 |
| 160 | CH(CH₃)₂ | OH | H | H | H | 300 |
| 161 | CH₂CH(CH₃)₂ | OH | H | H | H | 239 |
| 162 | CH(CH₃)₂ | COOH | H | H | H | 187 |
| 163 | CH(CH₃)₂ | SH | H | H | H | 210 |
| 164* | —(CH₂)₂O(CH₂)₂— | NHCH₂CH(CH₃)₂ | (see R¹) | H | H | 83 |
| 165 | COCH₃ | H | H | H | H | 190 |
| 166 | COCH₃ | H | COCH₃ | H | H | 103 |
| 167 | CH(CH₃)₂ | H | COCH₃ | H | H | 81–84 |
| 168 | n-C₃H₇ | H | COCH₃ | H | H | 48–53 |
| 169 | CH₂CH(CH₃)₂ | OH | COCH₃ | H | H | 147 |
| 170 | Hydrochloride salt of Compound No. 5 above | | | | | |
| 171 | Hydrochloride salt of Compound No. 104 above | | | | | |

*Compounds No 144 and 164 have a combined R¹ and R³ bridging group, shown complete under R¹

| Compound No. | R¹ | R² | R³ | R⁵ | R⁶ | m.p. °C. |
|---|---|---|---|---|---|---|
| 172 | CH(CH₃)C₆H₅ | CH₃ | H | H | H | 129 |
| 173 | CH(CH₃)₂ | C₂H₅ | H | H | H | 111 |
| 174 | CH(CH₃)(CH₂)₁₀CH₃ | H | H | H | H | 64 |
| 175 | CH₂—[tetrahydrofuran-2-yl] | H | H | H | H | 93 |
| 176 | (CH₃)₂ | H | NH₂ | H | H | 124 (chloride) |
| 177 | N(CH₃)₂ | H | H | H | H | 157 |
| 178 | CH(CH₃)₂ | H | H | CH₃ | CH₃ | 126 |
| 179 | CH(CH₃)(CH₂)₂CH₃ | H | H | CH₃ | CH₃ | 113 |
| 180 | CH(CH₃)C₆H₅ | H | H | CH₃ | CH₃ | 105 |
| 181 | CH(CH₃)(CH₂)₄CH₃ | H | H | CH₃ | CH₃ | 71 |
| 182 | CH(CH₃)C₆H₅ | C₆H₅ | H | H | H | 132 |
| 183 | CH(CH₃)CH₂CN | H | H | H | H | 131 |
| 184 | [isobutyl sulfone ring] | H | H | H | H | 195 |

TABLE 1-continued

| Compound No. | R¹ | R² | R³ | R⁵ | R⁶ | m.p. °C. |
|---|---|---|---|---|---|---|
| 185 | $CH(C_2H_5)(CH_2)_3CH_3$ | H | H | H | H | 108 |
| 186 | $CH(CH_3)_2$ | H | H | H | $NHCOCH_3$ | 319 |
| 187 | $(CH_2)_5$ | H | $NH_2$ | H | H | 156 (chloride) |
| 188 | $C(CH_3)_2CH_2OH$ | H | H | H | H | 226 |
| 189 | $CH(C_2H_5)CH_2CH(CH_3)C_2H_5$ | H | H | H | H | 131 |
| 190 | $CH[(CH_2)_3CH_3]_2$ | H | H | H | H | 136 |
| 191 | N⟨piperidino⟩ | H | H | H | H | 206 |
| 192 | $CH(CH_3)_2$ | $CH(CH_3)_2$ | H | H | H | 89 |
| 193 | $CH(CH_3)(CH_2)_2CH_3$ | Cl | H | H | H | 131 |
| 194 | $CH(CH_3)(CH_2)_2CH_3$ | $CH(CH_3)_2$ | H | H | H | 94 |
| 195 | $CH(CH_3)(CH_2)_4CH_3$ | $CH(CH_3)_2$ | H | H | H | [b.p. 150° (bath)/0.01 mm] |
| 196 | $(CH_2)_2CH_3$ | $CH(CH_3)_2$ | H | H | H | 75 |
| 197 | $CH(CH_3)C_6H_5$ | $CH(CH_3)_2$ | H | H | H | 123 |
| 198 | $CH[(CH_2)_4CH_3]_2$ | H | H | H | H | 89 |
| 199 | $CH(CH_3)(CH_2)_3CH_3$ | $CH_3$ | H | H | H | 118 |
| 200 | $CH(CH_3)(CH_2)_2CH(CH_3)_2$ | $CH_3$ | H | H | H | 122 |
| 201 | $CH(CH_3)C(CH_3)_3$ | Cl | H | H | H | 157 |
| 202 | $CH(CH_3)_2$ | $CH_3$ | H | $CH_3$ | H | 55 |
| 203 | $CH(CH_3)C_6H_5$ prepared (−) amine; S configuration | $CH_3$ | H | H | H | 119 |
| 204 | $CH(CH_3)(CH_2)_4CH_3$ | Cl | H | H | H | 91 |
| 205 | $CH(CH_3)(CH_2)_3CH(CH_3)_2$ | $CH_3$ | H | H | H | 113 |
| 206 | $CH(CH_3)(CH_2)_5CH_3$ | $CH_3$ | H | H | H | 109 |
| 207 | $CH(CH_3)(CH_2)_6CH_3$ | $CH_3$ | H | H | H | 89 |
| 208 | $CH(CH_3)(CH_2)_7CH_3$ | $CH_3$ | H | H | H | 72 |
| 209 | salt of Compound No 5 with sulphuric acid | | | | | 161 |
| 210 | salt of Compound No 5 with nitric acid | | | | | 147 |
| 211 | salt of Compound No 40 with hydrochloric acid | | | | | 173 |
| 212 | $CH(CH_3)(CH_2)_2CH_3$ | $CH_3$ | H | $CH_3$ | H | [b.p. 165° (bath)/0.01 mm] |
| 213 | salt of Compound No 40 with nitric acid | | | | | 115 |
| 214 | $CH(CH_3)(CH_2)_4CH_3$ | $CH_3$ | H | $CH_3$ | H | [b.p. 175° (bath)/0.01 mm] |
| 215 | salt of Compound No 5 with phosphoric acid | | | | | 211 |
| 216 | salt of Compound No 5 with toluene p-sulphonic acid | | | | | 168 |
| 217 | $CH(CH_3)(CH_2)_2CH_3$ | H | H | $CH_3$ | H | 79 [b.p. 165° (bath)/0.02 mm] |
| 218 | $CH[(CH_2)_8CH_3]_2$ | H | H | H | H | [b.p. 200° (bath)/0.03 mm] |
| 219 | salt of Compound No 5 with methanesulphonic acid | | | | | oil |
| 220 | salt of Compound No 5 with trichloroacetic acid | | | | | oil |
| 221 | salt of Compound No 40 with sulphuric acid | | | | | 100 |
| 222 | salt of Compound No. 40 with toluene p-sulphonic acid | | | | | oil |
| 223 | $4-CH_3-C_6H_4$ | H | H | H | H | 166 |
| 224 | $4-Cl-C_6H_4$ | H | H | H | H | 157 |
| 225 | $CH_2C_6H_5$ | H | $NH_2$ | H | H | 149 |
| 226 | salt of compound No 40 with phosphoric acid | | | | | 216 |
| 227 | $CH(CH_3)(CH_2)_8CH_3$ | H | H | H | H | 73 |
| 228 | $CH(CH_3)(CH_2)_4CH_3$ | $4-Cl-C_6H_4$ | H | H | H | 105 |
| 229 | $CH(CH_3)_2$ | $4-Cl-C_6H_4$ | H | H | H | 155 |
| 230 | $(CH_2)_6NH$-⟨thienopyrimidine⟩ | H | H | H | H | 194 |
| 231 | $CH(CH_3)(CH_2)_2CH(CH_3)(CH_2)_2CH_3$ | H | H | H | H | 53 [b.p. 160° (bath)/0.02 mm] |
| 232 | $CH(CH_3)(CH_2)_{11}CH_3$ | H | H | H | H | 69 [b.p. 170° (bath)/0.04 mm] |
| 233 | $CH(CH_3)C_6H_5$ prepared from (−) amine; S configuration | $C_2H_5$ | H | H | H | 137 |
| 234 | $CH(CH_3)(CH_2)_2CH_3$ | $4-Cl-C_6H_4$ | H | H | H | 120 |
| 235 | $CH(CH_3)(CH_2)_2CH_3$ | H | H | H | Br | 183 |
| 236 | $CH(CH_3)_2$ | H | H | H | Br | 186 |
| 237 | $CH(CH_3)C_6H_5$ | $CH_3$ | H | $CH_3$ | H | 119 |

TABLE 1-continued

| Compound No. | R¹ | R² | R³ | R⁵ | R⁶ | m.p. °C. |
|---|---|---|---|---|---|---|
| 238 | CH(CH₃)C₂H₅ | C₂H₅ | H | H | H | [b.p. 210° (bath)/0.01 mm] 109 |
| 239 | CH(CH₃)(CH₂)₂CH₃ | C₂H₅ | H | H | H | [b.p. 175° (bath)/0.04 mm] |
| 240 | CH(CH₃)(CH₂)₄CH₃ | C₂H₅ | H | H | H | [b.p. 190° (bath)/0.04 mm] |
| 241 | CH(CH₃)(CH₂)₄CH₃ | H | H | H | Br | 153 |
| 242 | CH(CH₃)C₆H₅ | H | H | H | Br | 182 |
| 243 | CH(CH₃)CO₂H | H | H | H | H | 175 |
| 244 | (CH₂)₃N(CH₃)₂ | H | H | H | H | [b.p. 150° (bath)/0.04 mm] |
| 245 | CH(C₂H₅)(CH₂)₅CH₃ | H | H | H | H | 84 [b.p. 160° (bath)/0.05 mm] |
| 246 | CH(CH₃)(CH₂)₃CH₃ | C₂H₅ | H | H | H | 83 [b.p. 160° (bath)/0.06 mm] |
| 247 | CH(CH₃)(CH₂)₁₆CH₃ | H | H | H | H | 73 |
| 248 | CH(CH₃)(CH₂)₂CH(CH₃)₂ | C₂H₅ | H | H | H | 89 |
| 249 | CH(CH₃)(CH₂)₂CH₃ | C₂H₅ | H | H | H | 81 |
| 250 | CH(CH₃)₂ | H | H | H | (CH₃)₂NSO₂ | 202 |
| 251 | CH(CH₃)(CH₂)₂CH₃ | H | H | H | (CH₃)₂NSO₂ | 132 |
| 252 | CH(CH₃)(CH₂)₄CH₃ | H | H | H | (CH₃)₂NSO₂ | 135 |
| 253 | CH(CH₃)C₆H₅ | H | H | H | (CH₃)₂NSO₂ | 235 |
| 254 | CH(CH₃)₂ | SCH₂CONH₂ | H | H | H | 186 |
| 255 | (CH₂)₆CH₃ | H | CH₃ | H | H | Oil; pmr δ3.4(NCH₃) |
| 256 | —CH=CH—CH=CH— | H | see R¹ | H | H | 70 (HCl salt) |
| 257 | (CH₂)₉CH₃ | H | CH₃ | H | H | Oil; pmr δ3.35(NCH₃) |
| 258 | (CH₂)₁₀CH₃ | H | H | H | H | |
| 259 | (CH₂)₈CH₃ | H | H | H | H | |
| 260 | CH(CH₃)—⟨S⟩ | H | H | H | H | |
| 261 | CH(CH₃)—⟨O⟩ | H | H | H | H | |
| 262 | CH(CH₃)(CH₂)₅CH₃ | Cl | H | H | H | |
| 263 | (CH₂)₈CH=CH(CH₂)₇CH₃ | H | H | H | H | |
| 264 | CH(CH₃)(CH₂)₂CH=C(CH₃)₂ | H | H | H | H | |

In the foregoing Table the following groups of compounds are preferred groups. Group (i) compounds are preferred over Group (ii) compounds which in turn are preferred over Group (iii) compounds.
(i) 78, 92, 102, 107, 108 and 208;
(ii) 20, 35, 40, 56, 76, 93, 95, 109, 174, 185, 207, 212, 214, 217, 227, 231 and 259;
(iii) 6, 18, 30, 49, 53, 57, 89, 117, 128, 164, 173, 181, 198, 200, 202, 205, 206, 232, 247, 258 and 261.

The compounds may be prepared either by:
(a) treating an appropriately substituted 2-amino-3-cyanothiophene with an orthoester, or a Vilsmeier reagent (e.g. N-N-dimethylformamide/phosphorus oxychloride), then an amine and rearranging the product, if necessary, with a strong base such as sodium alkoxide;

(b) reacting a thieno[2,3-d]pyrimidine containing a labile function (e.g. halo, mercapto, alkylthio, alkanesulphonyl) with an amine or a salt thereof;

(c) treating a 4-aminothieno[2,3-d]pyrimidine, if necessary under basic conditions, with a compound having an electrophilic cen tre;

(d) subjecting a compound prepared as described above under (a), (b) or (c) to further reaction for example by replacement of halogen at C-2, nitration or halogenation of thiophene ring;

(e) treating 4-unsubstituted- or 4-monosubstituted-amino derivatives with acid halides or acid anhydrides, especially under basic conditions to give 4-acylamino thieno[2,3-d]pyrimidines; or (f) subjecting 4-acylaminothieno[2,3-d]pyrimidines prepared as described above under (e) to reduction to give 4-(alkyl substituted amino) thieno[2,3-d]pyrimidines.

In the process of the invention the compounds are preferably used in the form of a composition which comprises an inert carrier. The carrier may comprise solids in the form of dusting powders or granules or shaped polymeric materials through which the active ingredient is capable of migrating. Preferably the carrier is an aqueous liquid formulation.

The liquid formulations, which may be used as dips or sprays, are generally aqueous dispersions or emulsions containing the active ingredient in the presence of one or more wetting agents, dispersing agents, emulsifying agents or suspending agents. Emulsifiable solutions or suspensions of the active compound may be prepared by dissolving or suspending it in a solvent, or mixture of solvents, which is not harmful to the media to be treated, adding an emulsifier and/or wetting agent and optionally, adding some water. Suitable solvents are, for example, ethylene dichloride, isopropyl alcohol, propylene glycol, diacetone alcohol, toluene, xylenes, kerosene, cyclohexanone, methylnaphthalene and trichloroethylene.

Solid formulations, which may be used as dusting powders or granules, are generally compositions wherein the active ingredient is mixed with a solid diluent or carrier. Suitable solid diluents or carriers may be, for example, kaolinite (china clay), montmorillonite, attapulgite, talc, pumice, silica, calcium carbonate, gypsum, powdered magnesia, Fuller's earth, Hewitt's earth and diatomaceous earth.

Solid compositions may also be in the form of dispersible powders or grains comprising, in addition to the active ingredient, a wetting agent to facilitate the dispersion of the powder or grains in liquids. Such powders or grains may include fillers, suspending agents and the like. The compositions may also be in the form of aqueous pastes.

The compositions may also be in the form of capsules or microcapsules containing either the active ingredient itself, or a composition containing the active ingredient, and prepared by any of the known encapsulation or microencapsulation techniques.

By the inclusion of suitable additives, for example, for improving the distribution, adhesive power and resistance to rain on treated surfaces, the different compositions can be better adapted for the various uses for which they are intended.

Solid compositions may also be in the form of solid shaped articles comprising a mixture of the active ingredient and a polymeric material from which the active ingredient can migrate. Such shaped articles are of particular use when in the form of bands, collars, and especially ear- and tail-tags, for attachment to the animal to be treated. Suitable polymeric materials include, for example, the lower polyolefins, poly(vinyl chloride), poly(vinyl fluoride), poly(chlorotrifluoroethylene), polyurethanes, polycarbonate, polyesters including poly(ethylene terephthalate), poly(vinylidene chloride), poly(benzimidazole), ethylene-acrylic acid copolymer ionomers, cellulose acetate, regenerated cellulose film, polystyrene and etc. Alternatively solid compositions may be in the form of solid shaped articles comprising the active ingredient or a composition containing the active ingredient enclosed within a polymeric wall element through which the active ingredient can migrate. Suitable polymeric wall elements include the polymeric materials listed above and laminates of those polymeric materials.

The compositions which are to be used in the form of aqueous dispersions or emulsions are generally supplied in the form of a concentrate containing a high proportion of the active ingredient or ingredients, the said concentrate to be diluted with water before use.

These concentrates are often required to withstand storage for prolonged periods and after such storage, to be capable of dilution with water in order to form aqueous preparations which remain homogeneous for a sufficient time to enable them to be applied by conventional spray equipment. The concentrates may conveniently contain from 10-85% by weight of the active ingredient or ingredients and generally from 25-60% by weight of the active ingredient or ingredients. When diluted to form aqueous preparations, such preparations may contain varying amounts of the active ingredient or ingredients depending upon the purpose for which they are to be used, but an aqueous preparation containing between 0.0001% and 5.0% by weight of the active ingredient or ingredients may be used.

Suitable dose rates of the active ingredient for the control of infestations of Ixodid tick are not narrowly critical and are dependent to some extent on the Ixodid tick being treated. Rates will also be related to the mode of application of the active ingredient, for example the rate will vary for each type of application such as dipping, spraying or dusting of the infested surface. As a general guide for the treatment of cattle infested by *Boophilus microplus* dips containing up to 5% w/w of active ingredient are satisfactory for most degrees of severity of infestation by "resistant" strains of tick and adequate control may be effected in many instances where the concentration of active ingredient in a dip is in the range from 0.005% to 1.0% w/w.

Liquid formulations, preferably concentrated liquid formulations, may also be applied to the media to be treated as a "pour-on" formulation. This technique is especially applicable to the treatment of animals such as cattle as the active ingredient is generally rapidly dispersed over the animal's body by tail and head movement.

It is to be understood that the tickicidal compositions used in the process of this invention may comprise, in addition to one or more compounds from the class of compounds described, one or more other compounds having biological activity.

The invention is illustrated, but not limited, by the following Examples, in which degrees of temperature signified by ° are expressed in degrees Centigrade.

EXAMPLE 1

This Example illustrates the preparation of compound nos. 1-15 of Table 1.

A mixture of an optionally substituted 2-amino-3-cyanothiophene (2.48 g) and triethylorthoformate (50 ml) was refluxed for four hours, then excess ester removed in vacuo. The residue was treated with a solution of an amine (excess) in ethanol, stirred overnight at room temperature, evaporated to dryness, then dissolved in dimethylformamide (50 ml) containing methanolic sodium methoxide (1 ml from 0.06 g sodium). The solution was stirred for one hour at 85°-95°, evaporated in vacuo, diluted with water and the product either removed by filtration or extracted into chloroform. Melting-points are shown in Table 1.

Certain examples (e.g. Compound Nos. 8 and 9) give mixtures of endo- and exo-alkylated products under standard conditions but further isomerization to the desired exo-isomer can be achieved by more vigorous methoxide treatment. In other cases (e.g. Compound No. 1), the alkoxide treatment can be omitted.

EXAMPLE 2

This Example illustrates the preparation of Compound nos 5, 17, 40, 172 and 177 of Table I.

A mixture of 2-amino-3-cyanothiophene (30 g) and a triethylorthoester (90 ml) was heated on a steam bath for 90 minutes, evaporated and distilled to give the 2-ethoxymethyleneamino-3-cyanothiophene (e.g. 2-H, 37.4 g, m.p. 38°, b.p. 104°-9°/0.05 mm; 2-CH$_3$, 40.0 g, b.p. 78°-82°/0.01 mm). The appropriate product was treated with an amine or hydrazine (see Example 7), anhydrous sodium acetate and acetic acid and the mixture heated (90°-150°) until reaction complete (e.g. 30 minutes to 48 hours). The mixture was cooled, diluted with water and the product either removed by filtration or extracted into a solvent (e.g. ether). Following recrystallisation from a suitable solvent, the products had melting-points as shown in Table 1.

EXAMPLE 3

This Example illustrates the preparation of Compound No. 243 of Table 1.

Examples 1 and 2 could not be made to operate where the variable amine also contained an acid function e.g. an amino-acid. The following modification was successful.

A mixture of DL-alanine (9.0 g), 2-ethoxymethyleneamino-3-cyanothiophene (4.0 g, prepared as described in Example 2) and 5 N sodium hydroxide solution was heated to 45°, then allowed to cool slowly for 30 minutes. It was then cooled to 0° and the precipitate filtered off and treated with a further quantity of 5 N sodium hydroxide solution (12 ml) at 100° for 8 minutes. The mixture was cooled, acidified to pH 5 with dilute hydrochloric acid and the precipitate filtered off, washed with a little water and recrystallised from aqueous ethanol to give the title compound (1.03 g, m.p. 175°).

EXAMPLE 4

This Example illustrates the preparation of 4-isopropylaminothieno[2,3-d]pyrimidine (Compound No. 5) by an alternative procedure to that described in Examples 1 and 2.

A mixture of sodium hydride (0.64 g, 100%), 4-aminothieno[2,3-d]pyrimidine (3.5 g) and dry dimethylformamide (25 ml) was stirred for fifteen minutes at <20°, then treated with 2-iodopropane (3.5 ml). After stirring at <20° for ninety minutes, the reaction mixture was diluted with water and cooled in ice. The precipitate was washed with water, dried and recrystallised from acetonitrile to give the title compound (1.4 g, m.p. 225°–6°).

EXAMPLE 5

This Example illustrates the preparation of a number of 4-aminothieno[2,3-d]pyrimidines by an alternative procedure to those described in Examples 1, 2 and 4. By this procedure compounds nos. 1–3, 5, 12 and 16–128, 172–175, 178–185, 188–190, 192, 194–200, 202–203, 205–208, 212, 214, 217–218, 223–224, 227–234, 237–240, 244–249, 255–261, 263 and 264 were prepared.

A mixture of an appropriately substituted 4-chlorothieno[2,3-d]pyrimidine and either a primary or secondary amine*, neat or together with a solvent (e.g. a lower alcohol, particularly ethanol), was allowed to react for one-half to twenty hours at 20° C. to 160° C. depending on the nature of the reagents. It was then diluted with water** and the product either removed by filtration or extracted into chloroform. Melting-points (after recrystallisation, or reprecipitation from acid) or boiling-points (bulb-tube distillation, bath temperature; shown in brackets) are shown in Table 1.

*The amine must either be used in excess (>2 equivalents) or in presence of at least one equivalent of a base e.g. triethylamine. Where the amine was available only as a hydrochloride, the mixture comprised the chloro compound (1 equivalent), amine hydrochloride (2 equivalents), 10 N aqueous sodium hydroxide solution (2 equivalents) and ethanol.
**In some cases, neutralisation with carbon dioxide at this stage is preferable.

EXAMPLE 6

This Example illustrates the preparation of several 4-hydrazinothieno[2,3-d]pyrimidines according to the invention (Compound Nos. 129–133 and 225, Table 1).

The appropriate 4-chloro derivative was treated with hydrazine or a monosubstituted derivative thereof, basically as described for amines in Example 5. Whilst only one product can be obtained in the case of hydrazine itself, substituted hydrazines could react on either nitrogen atom. In practice, reaction only at the more substituted position is observed. Melting-points are given in Table 1.

1,1-Disubstituted hydrazines react abnormally under these conditions. Thus, following reaction at the more substituted nitrogen atom, loss of either an alkyl group (1,1-dimethylhydrazine giving Compound No. 130) or an amino group (1-methyl-1-phenylhydrazine giving Compound No. 50) can occur. Alternative conditions leading to products containing the $NHNR_2$ moeity are described in Example 7.

EXAMPLE 7

This Example describes the preparation of several hydrazinium chlorides (Compounds Nos. 176 and 187) and their rearrangement to hydrazines (Compound Nos. 177 and 191).

4-Chlorothieno[2,3-d]pyrimidine (10 g) was added to an ice-cooled mixture of 1,1-dimethylhydrazine (9 ml) and acetonitrile (150 ml). The reaction mixture was allowed to stir at room temperature for 2¼ hours, and the precipitate filtered off, washed with acetonitrile and ether. The product (11.7 g, m.p. 124°) is Compound No. 176 of Table 1. Compound No. 187 was made similarly from 1-aminopiperidine.

A mixture of Compound No. 176 (5.0 g, prepared as described above), 1,5-diazabicyclo[4.3.0]non-5-ene (6 g) and acetonitrile (50 ml) was refluxed for one hour, evaporated and the residue partitioned between chloroform and ammonium chloride solution. The chloroform layer was washed, dried and evaporated and the residue washed with petrol, then recrystallised from acetonitrile to give Compound No. 177 (2.48 g, m.p. 157°). Compound No. 191 was prepared likewise from Compound No. 187.

Compound No. 177 can also be prepared by the method described in Example 2, using 1,1-dimethylhydrazine in place of the amine.

EXAMPLE 8

This example illustrates the preparation of several 4-amino-6-nitrothieno[2,3-d]pyrimidines according to the invention (Compounds Nos. 134 and 135 of Table 1).

A mixture of 4-isopropylaminothieno[2,3-d]pyrimidine (4.0 g, prepared as described in Example 5) and concentrated sulphuric acid (20 ml) was cooled to 0° and treated dropwise with a mixture of concentrated nitric acid (2.2 ml) and concentrated sulphuric acid (2.0 ml) whilst maintaining the temperature below 12° C. The mixture was allowed to stir at room temperature for a further one hour, poured into ice-water and neutralised with sodium carbonate. The precipitate was filtered off, washed with water and dried to give 4-isopropylamino-6-nitrothieno[2,3-d]pyrimidine (4.58 g, m.p. 200°) (Compound No. 134).

4-Diethylaminothieno[2,3-d]pyrimidine (2 g) was nitrated similarly to give the 6-nitro derivative (2.34 g, m.p. 135°) (Compound No. 135).

EXAMPLE 9

This Example illustrates the preparation of several 4-amino-6-nitrothieno[2,3-d]pyrimidines by an alternative procedure to that described in Example 8.

A mixture of 3,4-dihydrothieno[2,3-d]pyrimidin-4-one (21 g) and concentrated sulphuric acid (140 ml) was treated with mixture of concentrated nitric acid (15.4 ml) and concentrated sulphuric acid (14 ml) maintaining the temperature below 10° C. The mixture was stirred for a further hour at room temperature, poured into ice/water and the precipitate filtered off, washed with water and dried to give the 6-nitro derivative (24.6 g, m.p. 307°). A mixture of this material (15 g) and phosphorus oxychloride (200 ml) was refluxed for three hours, the excess reagent removed in vacuo and the residue treated with chloroform (400 ml) and ice-water (400 ml). The organic layer was washed with brine, dried and evaporated to give 4-chloro-6-nitrothieno[2,3-d]pyrimidine (16.9 g, m.p. 112°). Recrystallisation from acetonitrile gave material, m.p. 116°–118°.

Treatment of this chloro compound with amines (basically as described in Example 5) gave, for example, the 4-isopropylamino (m.p. 199°, Compound No. 134), and 4-benzylamino (m.p. 214°, Compound No. 136) derivatives.

EXAMPLE 10

This Example illustrates the preparation of 4-amino-6-nitrothieno[2,3-d]pyrimidines by an alternative procedure to that described in Examples 8 or 9.

Phosphorus oxychloride (5 ml) was added dropwise, with stirring, to dry N,N-dimethylformamide (20 ml) maintaining the temperature below 5° C. The solution was allowed to stand for fifteen minutes then treated, at 0°–5° C., with a suspension of 2-amino-3-cyano-5-nitrothiophene (5.1 g) in dry N,N-dimethylformamide (50 ml), allowed to attain room temperature, then kept at 20° C. for five days. It was then poured on to ice, the precipitate removed and the filtrate basified with ammonium hydroxide solution to give 2-dimethylaminomethyleneamino-3-cyano-5-nitrothiophene (m.p. 230°). A mixture of this material (0.5 g), benzylamine (0.26 g) and ethanol (100 ml) was refluxed for twelve hours, treated with acetic acid (0.5 ml) and heating continued for a further thirty minutes. The solvent was removed in vacuo and the residue diluted with water to give 4-benzylamino-6-nitrothieno[2,3-d]pyrimidine (0.4 g) (Compound No. 136).

EXAMPLE 11

This Example describes the preparation of 6-acetylamino-4-isopropylaminothieno[2,3-d]pyrimidine having the structural formula:

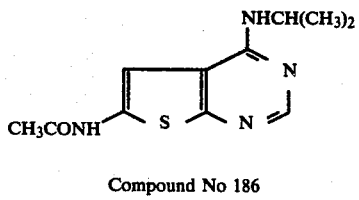

Compound No 186

A mixture of Compound No. 134 (3.0 g, prepared as described in Example 8), activated iron powder (4.8 g, prepared from zinc and ferrous sulphate), acetic anhydride (12 ml) and acetic acid (60 ml) was heated at 85° for 4 hours, cooled and poured into water. The precipitate was filtered off, dried and recrystallised from acetonitrile to give the title compound (1.37 g, m.p. 319°).

EXAMPLE 12

This Example illustrates the preparation of several 4-amino-2-chlorothieno[2,3-d]pyrimidines according to the invention. By this procedure Compound Nos. 137 to 144, 193, 201, 204 and 262 of Table 1 were prepared.

A mixture of 2-amino-3-carbonamidothiophene (100 g), sodium carbonate (106 g), ethyl chloroformate (140 ml) and ethanol (1.5 l) was heated at 40° for twenty minutes, filtered and poured into water (5 l) to give, after drying, 3-carbonamido-3-ethoxycarbonylaminothiophene (48.3 g, m.p. 195°). This material (45 g) was suspended in a solution of sodium carbonate (90 g) in water (900 ml), heated for two hours at 100°, cooled and acidified with hydrochloric acid to give 1,2,3,4-tetrahydrothieno[2,3-d]pyrimidin-2,4-dione (30 g, m.p. >300°). This material (45.0 g) was added slowly to phosphorus oxychloride (320 ml), followed by pyridine (45 ml), and the mixture refluxed for one hour. Excess phosphorus oxychloride was removed in vacuo, the residue poured, with stirring, into ice-water then extracted with chloroform. The extracts were evaporated to give 2,4-dichlorothieno[2,3-d]pyrimidine (34.2 g). After recrystallisation from petroleum (b.p. 80°–100° C.), this had m.p. 116°.

A mixture of this material and excess primary or secondary amine, either neat or together with a solvent, was allowed to react at room temperature for ten minutes. It was then diluted with water* and the product either removed by filtration or extracted with chloroform. Melting-points, after recrystallisation from a suitable solvent, are shown in Table 1.

*In some cases, neutralisation with carbon dioxide at this state is preferable.

EXAMPLE 13

This Example illustrates the preparation of several 2-substituted-4-aminothieno[2,3-d]pyrimidine according to the invention. By this procedure compounds nos. 145–164 and No. 254 of Table 1 were prepared.

The appropriate 2-chloro-4-aminothieno[2,3-d]pyrimidine, prepared as described in Example 12, was treated with the appropriate reagent(s) as shown in Table 2 to give the required derivative.

TABLE 2

| COMPOUND NO. (OF TABLE 1) | REACTION CONDITIONS (FROM COMPOUND NO. 137 OF TABLE 1 UNLESS OTHERWISE STATED) |
|---|---|
| 145 | imidazole, fusion, 100° |
| 146 | 1,2,4-triazole, fusion, 160° |
| 147 | NaOCH₃, methanol, reflux |
| 148 | hydrazine hydrate, ethanol, reflux |
| 149 | morpholine, reflux |
| 150 | pyrazole, fusion, 150° |
| 151 | Compound No. 148 + acetylactone |
| 152 | Compound No. 148 + nitrous acid |
| 153 | NaSCH₃, N,N-dimethylformamide |
| 154 | piperidine, reflux |
| 155 | Compound No. 153, two equivalents 3-chloroperbenzoic acid, chloroform |
| 156 | pyrrolidine, reflux |
| 157 | Compound No. 153, one equivalent 3-chloroperbenzoic acid chloroform |
| 158 | isobutylamine, reflux |
| 159 | sodium cyanide, dimethylsulphoxide, 140° |
| 160 | concentrated hydrochloric acid, reflux |
| 161 | Compound No 143, concentrated hydrochloric acid, reflux |
| 162 | Compound No. 159, 5N sodium hydroxide, ethanol, reflux |
| 163 | thiourea, hydrochloric acid, then sodium hydroxide solution |
| 164 | Compound No 144, isobutylamine, reflux |
| 254 | 2-mercaptoacetamide, potassium carbonate, ethanol, reflux |

EXAMPLE 14

This Example illustrates the preparation of 4-acetylaminothieno[2,3-d]pyrimidine having the structural formula:

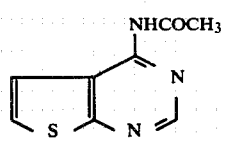

Compound No. 165

A mixture of 4-aminothieno[2,3-d]pyrimidine (7.55 g prepared as described in Example 1) and acetic anhydride (10 ml) was refluxed for 6 hours and evaporated in vacuo. The residue was recrystallised from ethanol to give the title compound (6.61 g, m.p. 189°–191°).

EXAMPLE 15

This Example illustrates the preparation of 4-diacetylaminothieno[2,3-d]pyrimidine having the structural formula:

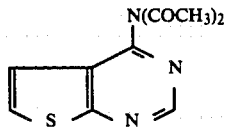

A mixture of 4-aminothieno[2,3-d]pyrimidine (4.53 g, prepared as described in Example 1), acetic anhydride (25 ml) and pyridine (50 ml) was refluxed for eighteen hours and evaporated to dryness. The residue was extracted with boiling cyclohexane (3×100 ml) and the extracts treated with charcoal, then filtered and cooled to give the title compound (2.04 g, 102°–104°).

EXAMPLE 16

This Example illustrates the preparation of several 4-acetylaminothieno[2,3-d]pyrimidines according to the invention. By this procedure compounds Nos. 167 and 168 were prepared.

A mixture of 4-isopropylaminothieno[2,3-d]pyrimidine (prepared as described in Example 5, 3.2 g), acetic anhydride (12 ml) and pyridine (25 ml) was refluxed for twenty-four hours, then evaporated to dryness. The residue was extracted with boiling cyclohexane and the extracts treated with charcoal, filtered and cooled to give the 4-acetylisopropylamino derivative (1.8 g, m.p. 81°–84°; Compound No. 167). The n-propylamino analogue, made similarly, had m.p. 48°–53°; (Compound No. 168).

EXAMPLE 17

This Example illustrates the preparation of 4-acetylisobutylaminothieno[2,3-d]pyrimidin-2-one, Compound No. 169, having the structural formula:

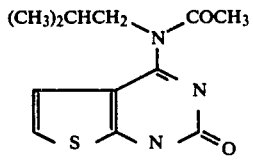

A mixture of 4-isobutylaminothieno[2,3-d]pyrimidin-2-one (Compound No. 161, prepared as described in Example No. 13, 3.5 g) and acetic anhydride (25 ml) was refluxed for eight hours and the excess reagent removed in vacuo. The residue was chromatographed on silica gel (dry column technique, ether) to give the 4-acetylisobutylamino-2-acetoxy derivative (1.3 g, m.p. 88°). This material (880 mg) was treated with a solution of sodium methoxide (from 100 mg of sodium) in methanol (20 ml) and allowed to stand for three days. The solvent was removed in vacuo and the residue treated with dilute hydrochloric acid. Extraction with chloroform gave the title compound (500 mg, m.p. 147°, Compound No. 169).

EXAMPLE 18

This Example illustrates the preparation of a number of salts of several 4-aminothieno[2,3-d]pyrimidines, having Compound Nos. 170, 171, 209–211, 213, 215–6, 219–222 and 226.

A mixture of the appropriate 4-amino derivative and excess organic or inorganic acid, either neat or in aqueous solution, was stirred, with heating if necessary, to give a homogeneous solution. The product was obtained either by cooling and filtration or evaporation to dryness. Melting-points, following recrystallisation are shown in Table 1.

EXAMPLE 19

This Example illustrates the preparation of several 4-amino-6-bromo-thieno [2,3-d] pyrimidines according to the invention (Compound Nos. 235–6, 241–2).

A mixture of 3,4-dihydrothieno[2,3-d]pyrimidine-4-one (21 g), bromine (30 ml) and acetic acid (300 ml) was stirred at room temperature for three hours, poured into water/ice (1 l) and the 6-bromo derivative filtered off and dried (18.2 g). A portion (17.0 g) was treated with thionyl chloride (230 ml) and N,N-dimethylformamide (3 ml) and refluxed for forty minutes. Excess acid chloride was removed in vacuo and the residue was partitioned between chloroform and water. The organic layer was washed, dried and evaporated to give 6-bromo-4-chlorothieno[2,3-d]pyrimidine (14.7 g). This was treated with a number of amines basically as described in Example 5.

EXAMPLE 20

This Example illustrates the preparation of several 4-amino-6-dimethylsulphonamidothieno[2,3-d]pyrimidines according to the invention (Compound Nos. 250–253).

3,4-Dihydrothieno [2,3-d] pyrimidin-4-one (50 g) was added portionwise to chlorosulphonic acid (243 ml), maintaining the temperature below 0° C. Thionyl chloride (121 ml) was added dropwise, and the mixture stirred for a further 30 minutes at room temperature; then two hours at reflux. It was then cooled, and poured carefully on to ice. The precipitate was washed and dried to give 6-chlorosulphonylthieno[2,3-d]pyrimidin-4-one (84 g). This compound (30 g) and dimethylamine (450 ml) were mixed at −10°, then allowed to stir at room temperature for two hours. The mixture was poured into water and acidified with hydrochloric acid. The precipitate was washed with water and ethanol, and dried to give the 6-dimethylsulphonamido-4-one (23.8 g). This material was converted into the 4-chloro derivative as described in Example 19 above and thence into the title compounds by treatment with amines basically as described in Example 5.

EXAMPLE 21

A suspension of each of the compounds of Table 3 was prepared by ball milling 10 parts of the compound with 985 parts of water and 5 parts of "Teric" N9 ("Teric" is a Registered Trade Mark and "Teric" N9 is a nonionic surfactant obtained by condensing nonylphenol with ethylene oxide in a molar ratio of 1:9) to give a composition containing 1.0% active ingredient. Portion of each of the above suspensions was then diluted with water to give compositions containing 0.1% and 0.01% active ingredient.

The efficacy of each of the compounds against engorged adult female ticks of the "Yeerongpilly" strain was tested by applying a microdrop of the appropriate concentration suspension to each of about twenty of the ticks. After 14 days the mortality count of the adult ticks was assessed by counting the eggs laid by them and the percentage of those eggs which had hatched. The results are given in Table 3.

The efficacy of each of the compounds against larval ticks of the "Yeerongpilly" strain was tested as follows: A sheet of filter paper was soaked in the appropriate concentration suspension and then allowed to dry. The treated paper was converted to the form of an envelope and approximately 100 larval ticks of the "Yeerongpilly" strain were enclosed therein. A mortality count was done on the larval ticks 48 hours after they had been placed in the envelope and the kill rated on a 0–5 scale wherein

| 0 | represents | 0–20%  | kill |
| 1 | represents | 20–50% | kill |
| 2 | represents | 50–80% | kill |
| 3 | represents | 80–95% | kill |
| 4 | represents | 95–99% | kill |
| 5 | represents | 100%   | kill |

The results are given in Table 3.

EXAMPLE 22

An emulsion of each of the compounds of Table 4 was prepared by mixing 25 parts of the compound with 75 parts of cyclohexanone and 25 parts of "Teric" N9 and diluting the mixture with water to provide the required concentration of active ingredient. Each of the emulsions so obtained was sprayed, to drippoint, onto calves heavily infested with various stages of the resistant "Biarra" strain of cattle tick. The efficacy of each of the compounds was assessed as follows:

(i) All adult female ticks which were fully engorged at the time of spraying were collected soon after spraying the calves. They were then placed in a Petri dish in an incubator for assessment of mortality based on capacity to lay eggs, and if eggs were laid, the viability of the eggs as shown by hatch of viable larvae. Engorged adults, if any, were also collected at 24 hours and 48 hours after spraying and the same assessment of mortality was made. This assessment is referred to as "Mortality—Engorged Adults" and the results, given in Table 4, are expressed as % mortality.

(ii) At daily intervals predetermined sampling areas on each calf were inspected for the effect of the active ingredient on the immature adults and nymphs. This assessment was rated on the 0–5 scale defined in Example 21 and is referred to as "mortality—Immature Adults" and "Mortality-Nymphs". The results are given in Table 4.

TABLE 3

IN VITRO ACTIVITY AGAINST ADULTS AND LARVAE

| Compound No | % Mortality of Adults | | Kill Rating against Larvae | | |
|---|---|---|---|---|---|
| | 1% a.i. | 0.1% a.i. | 1% a.i. | 0.1% a.i. | 0.01% a.i. |
| 4 | 10 | 0 | 5 | 0 | 0 |
| 6 | 100 | 0 | 5 | 5 | 0 |
| 11 | 100 | 0 | 5 | 5 | 0 |
| 16 | 10 | 0 | 5 | 5 | 0 |
| 18 | 10 | 0 | 5 | 5 | 0 |
| 20 | 100 | 0 | 5 | 5 | 0 |
| 22 | 10 | 0 | 5 | 0 | 0 |
| 23 | 0 | 0 | 5 | 5 | 0 |
| 24 | 0 | 0 | 3 | 0 | 0 |
| 25 | 0 | 0 | 5 | 5 | 0 |
| 26 | 0 | 0 | 3 | 0 | 0 |
| 27 | 0 | 0 | 4 | 1 | 0 |
| 28 | 10 | 0 | 5 | 0 | 0 |
| 29 | 0 | 10 | 4 | 1 | 0 |
| 30 | 0 | 0 | 4 | 4 | 0 |
| 32 | 10 | 0 | 5 | 1 | 0 |
| 33 | 0 | 0 | 5 | 5 | 0 |
| 34 | 0 | 0 | 4 | 2 | 0 |
| 35 | 20 | 0 | 5 | 4 | 0 |
| 36 | 0 | 0 | 5 | 4 | 0 |
| 39 | 20 | 0 | 5 | 5 | 0 |
| 40 | 10 | 0 | 5 | 5 | 0 |
| 41 | 70 | 0 | 5 | 4 | 0 |
| 43 | 0 | 0 | 5 | 0 | 0 |
| 44 | 0 | 0 | 5 | 5 | 0 |
| 45 | 0 | 0 | 5 | 4 | 0 |
| 49 | 0 | 0 | 5 | 4 | 0 |
| 53 | 100 | 0 | 4 | 0 | 0 |
| 54 | 0 | 0 | 4 | 1 | 0 |
| 56 | 20 | 10 | 5 | 5 | 0 |
| 57 | 30 | 0 | 5 | 5 | 0 |
| 58 | 10 | 0 | 5 | 5 | 0 |
| 59 | 0 | 0 | 3 | 0 | 0 |
| 62 | 100 | 0 | 0 | 0 | 0 |
| 68 | 0 | 0 | 5 | 4 | 0 |
| 74 | 0 | 0 | 4 | 2 | 0 |
| 76 | 100 | 0 | 5 | 5 | 0 |
| 77 | 0 | 0 | 2 | 0 | 0 |
| 78 | 90 | 10 | 5 | 5 | 0 |
| 79 | 30 | 0 | 4 | 0 | 0 |
| 80 | 0 | 0 | 1 | 0 | 0 |
| 82 | 0 | 0 | 5 | 5 | 0 |
| 85 | 0 | 0 | 4 | 1 | 0 |
| 87 | 60 | 0 | 5 | 5 | 0 |
| 89 | 60 | 10 | 5 | 5 | 2 |
| 92 | 30 | 20 | 5 | 5 | 2 |
| 93 | 30 | 0 | 5 | 5 | 0 |
| 94 | 10 | 0 | 5 | 2 | 0 |
| 95 | 0 | 0 | 5 | 5 | 0 |
| 96 | 0 | 0 | 5 | 3 | 0 |
| 97 | 0 | 0 | 5 | 0 | 0 |
| 98 | 0 | 0 | 2 | 0 | 0 |
| 99 | 0 | 0 | 5 | 0 | 0 |
| 100 | 0 | 0 | 5 | 5 | 0 |
| 101 | 0 | 0 | 5 | 5 | 0 |
| 102 | 90 | 20 | 5 | 5 | 0 |
| 107 | 40 | 10 | 5 | 5 | 2 |
| 108 | 20 | 10 | 5 | 5 | 0 |
| 109 | 10 | 0 | 4 | 1 | 0 |
| 112 | 0 | 0 | 3 | 0 | 0 |
| 113 | 0 | 0 | 5 | 0 | 0 |
| 114 | 0 | 0 | 5 | 2 | 0 |
| 115 | 0 | 0 | 5 | 4 | 0 |
| 116 | 0 | 0 | 4 | 0 | 0 |
| 117 | 20 | 30 | 5 | 5 | 0 |
| 125 | 0 | 0 | 5 | 0 | 0 |
| 127 | 0 | 0 | 2 | 0 | 0 |
| 128 | 0 | 0 | 5 | 5 | 0 |
| 129 | 20 | 0 | 0 | 0 | 0 |
| 137 | 0 | 0 | 3 | 0 | 0 |
| 139 | 0 | 0 | 5 | 0 | 0 |
| 143 | 0 | 0 | 5 | 3 | 0 |
| 146 | 20 | 10 | 0 | 0 | 0 |
| 147 | 0 | 0 | 3 | 0 | 0 |

TABLE 3-continued
IN VITRO ACTIVITY AGAINST ADULTS AND LARVAE

| Compound No | % Mortality of Adults 1% a.i. | % Mortality of Adults 0.1% a.i. | Kill Rating against Larvae 1% a.i. | Kill Rating against Larvae 0.1% a.i. | Kill Rating against Larvae 0.01% a.i. |
|---|---|---|---|---|---|
| 148 | 0 | 0 | 3 | 0 | 0 |
| 149 | 0 | 0 | 1 | 0 | 0 |
| 153 | 0 | 0 | 5 | 2 | 0 |
| 154 | 0 | 0 | 5 | 0 | 0 |
| 158 | 0 | 0 | 4 | 0 | 0 |
| 164 | 0 | 0 | 5 | 4 | 0 |
| 167 | 0 | 0 | 5 | 0 | 0 |
| 168 | 50 | 0 | 5 | 0 | 0 |
| 170 | 50 | 0 | 2 | 1 | 1 |
| 171 | 0 | 0 | 3 | 0 | 0 |
| 172 | 50 | 20 | 2 | 0 | 0 |
| 173 | 0 | 0 | 5 | 5 | 0 |
| 174 | 20 | 0 | 5 | 4 | 0 |
| 175 | 0 | 0 | 4 | 0 | 0 |
| 176 | 0 | 0 | 3 | 3 | 3 |
| 177 | 20 | 0 | 5 | 0 | 0 |
| 178 | 10 | 0 | 5 | 5 | 0 |
| 179 | 0 | 0 | 5 | 5 | 0 |
| 180 | 0 | 0 | 1 | 0 | 0 |
| 181 | 10 | 0 | 5 | 5 | 0 |
| 184 | 0 | 0 | 1 | 0 | 0 |
| 185 | 10 | 10 | 5 | 5 | 0 |
| 189 | 0 | 0 | 3 | 0 | 0 |
| 190 | 0 | 0 | 4 | 1 | 0 |
| 192 | 20 | 0 | 5 | 5 | 0 |
| 194 | 0 | 0 | 2 | 0 | 0 |
| 195 | 0 | 0 | 2 | 0 | 0 |
| 196 | 0 | 0 | 4 | 0 | 0 |
| 197 | 0 | 0 | 5 | 5 | 4 |
| 198 | 10 | 0 | 5 | 3 | 0 |
| 199 | 40 | 30 | 5 | 4 | 0 |
| 200 | 0 | 0 | 4 | 2 | 0 |
| 202 | 100 | 0 | 5 | 5 | 0 |
| 205 | 10 | 10 | 2 | 1 | 0 |
| 206 | 30 | 0 | 5 | 4 | 0 |
| 207 | 20 | 20 | 5 | 4 | 0 |
| 208 | 80 | 70 | 5 | 5 | 1 |
| 209 | 100 | 10 | 0 | 0 | 0 |
| 210 | 100 | 10 | 3 | 0 | 0 |
| 211 | 100 | 10 | 5 | 5 | 2 |
| 212 | 100 | 10 | 5 | 5 | 3 |
| 213 | 90 | 10 | 5 | 5 | 1 |
| 214 | 100 | 0 | 5 | 4 | 0 |
| 215 | 80 | 0 | 0 | 0 | 0 |
| 217 | 20 | 0 | 5 | 5 | 1 |
| 219 | 90 | 0 | 0 | 0 | 0 |
| 221 | 60 | 0 | 5 | 5 | 0 |
| 222 | 60 | 10 | 5 | 5 | 5 |
| 226 | 100 | 20 | 5 | 5 | 2 |
| 227 | 30 | 0 | 5 | 5 | 0 |
| 229 | 0 | 0 | 5 | 4 | 0 |
| 231 | 90 | 20 | 5 | 2 | 0 |
| 232 | 0 | 0 | 3 | 1 | 0 |
| 237 | 0 | 20 | 5 | 5 | 0 |
| 239 | 20 | 0 | 4 | 0 | 0 |
| 240 | 0 | 0 | 5 | 1 | 0 |
| 245 | 10 | 0 | 4 | 2 | 0 |
| 246 | 0 | 0 | 2 | 0 | 0 |
| 247 | 0 | 0 | 1 | 0 | 0 |
| 248 | 10 | 0 | 2 | 0 | 0 |
| 249 | 0 | 0 | 3 | 0 | 0 |
| 255 | 20 | 0 | 5 | 5 | 0 |
| 257 | 20 | 0 | 5 | 5 | 2 |
| 258 | 20 | 0 | 5 | 5 | 0 |
| 259 | 90 | 0 | 5 | 5 | 1 |
| 260 | 0 | 0 | 4 | 2 | 0 |
| 261 | 10 | 0 | 5 | 5 | 0 |
| 272 | 30 | 0 | 5 | 5 | 0 |

TABLE 4
IN VIVO ACTIVITY AGAINST ENGORGED ADULTS, IMMATURE ADULTS AND NYMPHS

| Compound No. | % Active Ingredient | Engorged Adults Mortality (%; <24 hr/24 hr/48 hr) | Immature Adults* | Nymphs* |
|---|---|---|---|---|
| 4 | 0.2 | 100/100/100 | 5 | 4 |
| 6 | 0.07 | —/40/—** | 4 | 5 |
| 20 | 0.25 |  | 4 | 4 |
| 20 | 0.125 | —/28/— | 3 | 3 |
| 35 | 0.25 | —/100/— | 5 | 4 |
| 40 | 0.20 | —/100/— | 5 | 4 |
| 56 | 0.25 | —/72/95 | 4 | 3 |
| 76 | 0.25 | 50/70/— | 4 | 4 |
| 78 | 0.25 |  | 5 | 5 |
| 78 | 0.125 | —/95/— | 4 | 5 |
| 78 | 0.07 | —/75/— | 3 | 0 |
| 92 | 0.15 | 50/100/60 | 4 | 2 |
| 92 | 0.075 | 90/85/— | 2 | 1 |
| 93 | 0.25 | —/50/— | 4 | 3 |
| 95 | 0.25 | —/75/— | 4 | 4 |
| 102 | 0.15 | 100/100/— | 5 | 5 |
| 102 | 0.075 | —/100/— | 4 | 3 |
| 107 | 0.25 | 100/100/— | 5 | 5 |
| 107 | 0.125 |  | 4 | 4 |
| 108 | 0.25 |  | 5 | 5 |
| 108 | 0.125 | —/80/— | 4 | 5 |
| 108 | 0.075 | —/60/— | 3 | 0 |
| 174 | 0.25 | —/90/— | 4 | 5 |
| 185 | 0.25 | —/80/— | 5 | 5 |
| 198 | 0.25 | —/20/— | 3 | 0 |
| 200 | 0.25 | 50/60/100 | 4 | 4 |
| 205 | 0.25 | 0/25/50 | 2 | 0 |
| 207 | 0.25 | —/100/— | 5 | 4-5 |
| 208 | 0.25 | —/—/— | 5 | 5 |
| 212 | 0.25 | —/—/— | 5 | 4 |
| 214 | 0.25 |  | 5 | 4 |
| 217 | 0.05 |  | 5 | 3 |
| 227 | 0.25 | —/100/— | 5 | 4 |
| 231 | 0.25 | —/100/— | 5 | 5 |
| 237 | 0.10 | 0/60/30 | 1 | 0 |
| 247 | 0.25 | —/50/— | 1 | 1 |
| 255 | 0.25 | —/—/— | 4 | 2 |
| 259 | 0.25 | 0/20/— | 3 | 5 |

*Kill rated on the same 0-5 scale used in Example 21
**A dash (—) means no engorged adult ticks were present

I claim:
1. A process for the prevention of infestation of an animal by Ixodid ticks, or for the control or eradication of infestations of Ixodid ticks on an animal, which process comprises applying to an animal which is infested with Ixodid ticks or subject to such infestation, an effective amount of a composition comprising as active ingredient a thienopyrimidine derivative of general formula I:

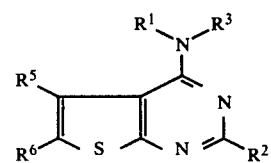

wherein
$R^1$ is chosen from alkyl or alkyl substituted with hydroxy, methoxy, cycloalkyl, aryl, heteroaryl, or heterocycloalkyl groups; alkenyl; alkynyl; cycloalkyl;
$R^3$ is chosen from hydrogen, alkyl and acyl; or $R^1$ and $R^3$ together form a saturated or unsaturated alkylene or heteroalkylene bridging group;

$R^2$ is chosen from hydrogen, hydroxy, mercapto, halo, cyano, amino, mono- or di-alkyl substituted amino, hydrazino, alkyl, alkenyl, alkynyl, alkoxy, alkylthio, cycloalkyl, aralkyl, aryl and trifluoromethyl;

$R^5$ and $R^6$ are independently chosen from hydrogen, alkyl, halogen and aryl;

or $R^5$ and $R^6$ together form a saturated alkyl bridging group; or an optical isomer thereof; or a tautomer thereof; or a salt thereof; and a carrier therefor.

2. A process according to claim 1 wherein in the thienopyrimidine of general formula I;

$R^1$ is chosen from straight or branched chain $C_1$ to $C_{20}$ alkyl or $C_1$ to $C_{20}$ alkyl substituted with at least one member of the group consisting of hydroxy and methoxy; $C_2$ to $C_{20}$ alkenyl; $C_2$ to $C_{20}$ alkynyl; $C_3$ to $C_8$ cycloalkyl; $C_3$ to $C_8$ cycloalkylmethyl; arylmethyl, 2-arylethyl and 1-arylethyl wherein aryl is chosen from furyl, thienyl, pyridyl, naphthyl, benzimidazolyl, phenyl or phenyl substituted with one or more substituents chosen from halogen, $C_1$ to $C_6$ alkoxy, and $C_1$ to $C_6$ alkyl;

$R^3$ is chosen from hydrogen, $C_1$ to $C_6$ alkyl and $C_1$ to $C_6$ alkanoyl;

or $R^1$ and $R^3$ together form a saturated or unsaturated alkylene bridging group or such alkylene bridging group in which one or more carbons are replaced by oxygen or nitrogen;

$R^2$ is chosen from hydrogen, hydroxy, mercapto, halo, cyano, $C_1$ to $C_6$ alkylamino, $C_2$ to $C_{12}$ dialkylamino, hydrazino, $C_1$ to $C_6$ alkyl, $C_1$ to $C_6$ alkoxy, $C_1$ to $C_6$ alkylthio, phenyl or phenyl substituted with one or more halogen atoms, and trifluoromethyl;

$R^5$ is chosen from hydrogen and $C_1$ to $C_6$ alkyl;

$R^6$ is chosen from hydrogen, $C_1$ to $C_6$ alkyl, halogen and phenyl;

or $R^5$ and $R^6$ together form a $C_2$ to $C_6$ alkylene bridging group.

3. A process according to claim 1 or claim 2 wherein in the thienopyrimidine of general formula I:

$R^1$ is chosen from straight or branched chain alkyl containing from 4 to 20 carbon atoms or such alkyl, substituted with hydroxy or methoxy, $C_4$ to $C_{20}$ alkenyl, and 1-phenylethyl;

$R^3$ is chosen from hydrogen, $C_1$ to $C_6$ alkyl and $C_1$ to $C_6$ alkanoyl;

$R^2$ is chosen from hydrogen, $C_1$ to $C_6$ alkyl and phenyl; and $R^5$ and $R^6$ are independently chosen from hydrogen and $C_1$ to $C_6$ alkyl.

4. A process according to any one of claims 1 to 3 inclusive wherein in the thienopyrimidine of general formula I:

$R^1$ is chosen from straight or branched chain alkyl containing from 4 to 20 carbon atoms;

$R^2$ and $R^3$ are chosen from hydrogen and methyl;

$R^5$ and $R^6$ are chosen from hydrogen and methyl provided that $R^6$ is methyl only when $R^5$ is methyl.

5. A process according to any one of claims 1 to 4 inclusive wherein in the thienopyrimidine of general formula I:

$R^1$ is chosen from straight or branched chain alkyl containing from 4 to 13 carbon atoms;

$R^2$ and $R^5$ are chosen from hydrogen and methyl; and $R^3$ and $R^6$ are each hydrogen.

6. A process according to any one of claims 1 to 5 inclusive wherein the thienopyrimidine of general formula I is the compound

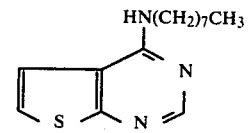

7. A process according to any one of claims 1 to 5 inclusive wherein the thienopyrimidine of general formula I is the compound

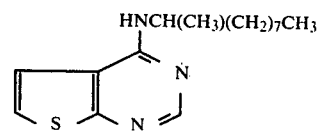

8. A process according to any one of claims 1 to 5 inclusive wherein the thienopyrimidine of general formula I is the compound

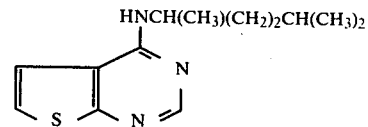

9. A process according to any one of claims 1 to 5 inclusive wherein the thienopyrimidine of general formula I is the compound

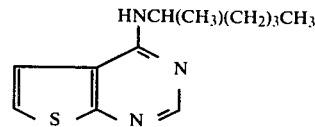

10. A process according to any one of claims 1 to 5 inclusive wherein the thienopyrimidine of general formula I is the compound

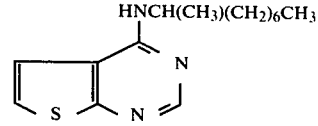

11. A process according to any one of claims 1 to 5 inclusive wherein the thienopyrimidine of general formula I is the compound

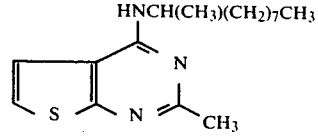

12. A process according to any one of claims 1 to 5 inclusive wherein the thienopyrimidine of general formula I is the compound

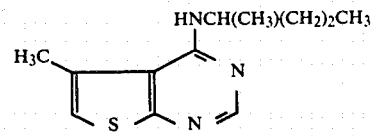

13. A process according to claim 1 which process comprises treating cattle to prevent infestation by, or to control or eradicate infestations of, the cattle tick *Boophilus microplus*.

14. A process according to claim 1 wherein the composition is applied by spraying.

15. A process according to claim 1 wherein the composition is applied by dipping.

16. A process according to claim 1 wherein the composition is applied in the form of a dusting powder.

17. A process according to claim 13 wherein the composition is applied in the form of a band, collar, ear-tag or tail-tag attached to the animal.

18. A process according to claim 14 wherein the spray is an aqueous composition comprising from 0.0001% to 5% by weight of active ingredient.

19. A process according to claim 15 wherein the dip is an aqueous composition comprising up to 5% by weight of active ingredient.

20. A process according to claim 19 wherein the active ingredient is in the range from 0.005% to 1% by weight.

* * * * *